United States Patent
Harrivel et al.

(10) Patent No.: US 9,848,812 B1
(45) Date of Patent: Dec. 26, 2017

(54) DETECTION OF MENTAL STATE AND REDUCTION OF ARTIFACTS USING FUNCTIONAL NEAR INFRARED SPECTROSCOPY (FNIRS)

(71) Applicant: The United States of America as represented by the Administrator of the National Aeronautics and Space Administration, Washington, DC (US)

(72) Inventors: Angela Harrivel, Cleveland, OH (US); Tristan Hearn, Cleveland, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 426 days.

(21) Appl. No.: 14/278,426

(22) Filed: May 15, 2014

Related U.S. Application Data (60) Provisional application No. 61/856,120, filed on Jul. 19, 2013.

(51) Int. Cl.
| | |
|---|---|
| *A61B 5/1455* | (2006.01) |
| *A61B 5/18* | (2006.01) |
| *A61B 5/145* | (2006.01) |
| *A61B 5/00* | (2006.01) |

(52) U.S. Cl.
CPC ............ *A61B 5/18* (2013.01); *A61B 5/1455* (2013.01); *A61B 5/14546* (2013.01); *A61B 5/725* (2013.01); *A61B 5/7207* (2013.01); *A61B 5/7282* (2013.01); *A61B 5/7405* (2013.01); *A61B 5/746* (2013.01); *A61B 5/747* (2013.01)

(58) Field of Classification Search
CPC . A61B 5/0059; A61B 5/1455; A61B 5/14551; A61B 5/14553; A61B 5/72; A61B 5/7203; A61B 5/7207
See application file for complete search history.

(56) References Cited

U.S. PATENT DOCUMENTS

| | | | |
|---|---|---|---|
| 6,167,298 A | 12/2000 | Levin | |
| 6,240,309 B1 * | 5/2001 | Yamashita | ......... A61B 5/14552 600/473 |
| 7,570,991 B2 | 8/2009 | Milgramm et al. | |
| 7,621,871 B2 | 11/2009 | Downs, III et al. | |
| 7,933,645 B2 | 4/2011 | Strychacz et al. | |
| 8,356,004 B2 | 1/2013 | Jung et al. | |

(Continued)

OTHER PUBLICATIONS

Abdelnour, A. Farras et al., "Real-time imaging of human brain function by near-infrared spectroscopy using an adaptive general linear model", Neuroimage, May 15, 2009, 46(1), pp. 133-143.*

(Continued)

*Primary Examiner* — Eric Winakur
(74) *Attorney, Agent, or Firm* — Robert H. Earp, III

(57) ABSTRACT fNIRS may be used in real time or near-real time to detect the mental state of individuals. Phase measurement can be applied to drive an adaptive filter for the removal of motion artifacts in real time or near-real time. In this manner, the application of fNIRS may be extended to practical non-laboratory environments. For example, the mental state of an operator of a vehicle may be monitored, and alerts may be issued and/or an autopilot may be engaged when the mental state of the operator indicates that the operator is inattentive.

20 Claims, 7 Drawing Sheets

(56) References Cited

U.S. PATENT DOCUMENTS

| | | |
|---|---|---|
| 2010/0081889 A1 | 4/2010 | Downs, III et al. |
| 2010/0185113 A1 | 7/2010 | Peot et al. |
| 2010/0292545 A1 | 11/2010 | Berka et al. |
| 2011/0161011 A1 | 6/2011 | Hasson et al. |
| 2012/0212353 A1 | 8/2012 | Fung et al. |
| 2012/0289869 A1 | 11/2012 | Tyter |
| 2012/0316793 A1 | 12/2012 | Jung et al. |

OTHER PUBLICATIONS

Hu, Xiao-Su et al., "Kalman estimator- and general linear model-based on-line brain activation mapping by near-infrared spectroscopy", BioMedical Engineering OnLine, 2010, 9:82, 15 pages.*

Cooper, Robert J., Selb, Juliette, Gagnon, Louis, Philip, Dorte, Schytze, Henrik W., Iversen, Messoud Ashina, Boas, David A., titled "A Systematic Comparison of Motion Artifact Correction Techniques for Functional Near-Infrared Spectroscopy", Frontiers in Neuroscience, Published Oct. 11, 2012, 10 pgs., vol. 6, Article 147, USA.

Harrivel, Angela, Hearn, Tristan, titled "Functional Near Infrared Spectroscopy: Watching the Brain in Flight", NASA's Aviation Safety Program and the Biomedical Engineering Department at the University of Michigan, 10 pgs., Chapter 20, NASA Glenn Research Center, Cleveland, OH USA.

Izzetoglu, Meltern, Chitrapu, Prabhakar, Bunce, Scott, Onaral, Banu, titled "Motion Artifact Cancellation in NIR Spectroscopy Using Discrete Kalman Filtering", BioMedical Engineering OnLine, 10 pgs., 2010, 9:16. USA.

\* cited by examiner

DETECTION OF MENTAL STATE AND REDUCTION OF ARTIFACTS USING FUNCTIONAL NEAR INFRARED SPECTROSCOPY (FNIRS)

The invention described herein was made by employees of the United States Government and may be manufactured and used by or for the Government for Government purposes without the payment of any royalties thereon or therefore.

The invention described herein was also made in the performance of work under a NASA contract and is subject to the provisions of Section 305 of the National Aeronautics and Space Action of 1958, Public Law 111-314, §3 (124 Stat. 3330; 51 U.S.C. Chapter 201).

CROSS REFERENCE TO RELATED APPLICATION

This application is a non-provisional of, and claims priority to, U.S. Provisional Patent Application Ser. No. 61/856,120 filed Jul. 19, 2013. The subject matter of this earlier-filed application is hereby incorporated by reference in its entirety.

ORIGIN OF THE INVENTION

FIELD

The present invention generally pertains to neuroimaging, and more specifically, to fNIRS that can be used in real time or near-real time and applies Kalman filtering to improve the detection of the mental state of individuals in practical operating environments.

BACKGROUND

Functional near infrared spectroscopy (fNIRS) is an emerging hemodynamic neuroimaging and brain-computer interface (BCI) technology that indirectly measures neuronal activity in the cortex via neuro-vascular coupling. fNIRS is non-invasive, relatively portable, relatively inexpensive, and safe for long term monitoring and repeated measurements. fNIRS quantifies hemoglobin concentration ([Hb]) changes in the brain based on optical intensity measurements. More specifically, fNIRS quantifies [Hb] changes with time based on optical intensity measurements of light that has scattered through the outer layers of the cortex beneath the optical probe. fNIRS measures the same hemodynamic changes as the functional magnetic resonance imaging (FMRI) blood oxygen level dependent signal, with lower spatial resolution but improved temporal resolution. Hemodynamic activations can be detected across the whole head with use of a sufficient number of probes placed in enough locations. Cognitive state is determined via pattern classification of the functional activations.

fNIRS works relatively well in a laboratory environment and has been used in many neuroscientific research studies, including real-time classification of state using an extended Kalman filter and known stimulus timing. However, conventional fNIRS techniques do not work well outside of the laboratory environment. Accordingly, fNIRS techniques suitable for practical applications outside of the laboratory environment may be beneficial.

SUMMARY

Certain embodiments of the present invention may be implemented and provide solutions to the problems and needs in the art that have not yet been fully solved by conventional neuroimaging techniques. For instance, in some embodiments, fNIRS can be used in real time or near-real time to detect the mental state of individuals. Phase measurement can be applied to drive an adaptive filter for the removal of motion artifacts in real time or near-real time. Such embodiments may extend the application of fNIRS to practical non-laboratory environments.

In one embodiment of the present invention, a computer-implemented method includes receiving, by a computing system, data pertaining to hemoglobin [Hb] levels in an individual's brain. The computer-implemented method also includes determining, by the computing system, presence of a potential artifact based on a phase shift in the data measured using frequency domain fNIRS instrumentation by comparing a signal intensity of a source signal to a detected signal intensity. The computer-implemented method further includes determining, by the computing system, whether changes in the hemoglobin levels and changes in the phase shift are correlated to confirm that the potential artifact is an artifact. Additionally, the computer-implemented method includes reducing or removing the artifact, by the computing system, using Kalman filtering when the changes in the hemoglobin levels and changes in the phase shift are correlated.

In another embodiment of the present invention, a computer program is embodied on a non-transitory computer-readable medium. The program is configured to cause at least one processor to receive data pertaining to hemoglobin [Hb] levels in an individual's brain and analyze a mental state of the individual based on the measured [Hb] levels in the individual's brain. The computer program is also configured to cause the at least one processor to determine whether the mental state indicates that the individual is attentive enough to perform a task.

In yet another embodiment of the present invention, a system includes a sensor array configured to provide analog data pertaining to hemoglobin [Hb] levels in an individual's brain. The system also includes a microcontroller configured to receive the analog data from the sensor array and convert the analog data into digital data. The system further includes a computing system configured to receive the digital data from the microcontroller. The computing system is also configured to determine presence of a potential artifact based on a phase shift in the data measured using the sensor array by comparing a signal intensity of a source signal to a detected signal intensity. The computing system is further configured to determine whether changes in the hemoglobin levels and changes in the phase shift are correlated to confirm that the potential artifact is an artifact. Additionally, the computing system is configured to reduce or remove the artifact using Kalman filtering when the changes in the hemoglobin levels and changes in the phase shift are correlated.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments of the present invention pertain to fNIRS that can be used in real time or near-real time to detect the mental state of individuals. Practical applications include, but are not limited to, pilots, astronauts, truck drivers, heavy equipment operators, and clinical outpatients. Implementation for monitoring outside the laboratory generally requires techniques that are appropriate for use by lay persons. Also, implementation of fNIRS for such practical applications has been hindered due to the lack of a way to remove motion artifacts, for which no standard processing method previously existed. Motion artifacts can be significant, and are likely to occur in operational environments. Practical non-laboratory applications should have algorithms and filters automating bad channel detection and performing dynamic artifact removal.

Bad channels can be automatically detected based on the variance or amount of artifacts in the signal they provide, including a highly varying phase signal. Once detected, the bad channel signal should be filtered to remove or reduce the artifact, or the signal should be left out of further analysis. This improves detection of the individual's true mental state.

Frequency domain (FD) instruments for (NIRS measure radio frequency (RF)-modulated signal intensity amplitude and offset, plus phase shift of the detected optical intensity signal relative to that of the source. The phase shift data provide a direct indication of the coupling noise associated with signal detection, and thus, the quantification of [Hb] at that time for that channel. This phase measurement can be applied to drive an adaptive filter for the removal of motion artifacts in real time or near-real time.

Such embodiments may make it possible to watch the activations within the brain of a pilot during the safety-critical task of flying, for example. Importantly, this is distinct from the use of vigilance tests that the pilot could undergo only while breaking from the task at hand. Such "fit-to-fly" tests may be passed due to short-term increases in attentional effort, which may not be sustainable for long flight durations. During monitoring, information regarding cognitive state could be used to trigger appropriate risk mitigations in real time via changes in flight automation and information display. Vehicles that the operator may be operating include, but are not limited to, aircraft, spacecraft, cars, trucks, ships, and industrial vehicles.

Some embodiments focus on improving techniques for applying fNIRS to in-task operator characterization. Optical sensing may improve upon the existing use of other modalities for operator characterization, especially through combination therewith. Examples include, but are not limited to, electroencephalography and other physiological measures used for augmented cognition, operator performance research, and crew cognition research.

Some embodiments employ a new filtering method based on the FD phase measurement for real time or near-real time signal quality detection and improvement. It is generally desirable to reduce the impact of motion and poor optical coupling of probes to the skin since such artifacts degrade signal quality, and thus, cognitive state classification accuracy. Kalman filters may be used to estimate real signals based on measurements in real time. Such filters may be tuned depending on the current state of the process being estimated. The FD phase signal provides a measurement of the noise in the fNIRS hemodynamic measurements. Thus, the phase may be an appropriate and natural choice for such a tuning parameter in some embodiments.

The tuning determines how much of a given artifact is removed by the filter and how significantly the signal is affected by the filter when no artifact is being removed. The phase is used as one parameter (R) through which the tuning is controlled. The phase gives an indication of how much of a given artifact is in the signal. No auxiliary sensors are required to measure the phase shift, and thus to quantify artifacts in the signal. When no artifact is detected, R is low, and the filter is turned "off." If the second parameter (Q) is high (i.e., greater than 0.0001), the process minimally affects the signal. Parameter high Q allows the output signal to change more quickly when the input signal changes.

After filtering, the output signal will generally have contributions from motion and poor coupling reduced or removed, thus leaving a signal more indicative of changes that are due to hemodynamic brain activations of interest. Cognitive state classification based on these signals should more reliably reflect brain activity. Optical intensity is attenuated by absorption and scattering along the optical path length, which is the path light travels through the head from the source to the detector. The phase is sensitive to motion because of its dependence on the separation between the source and the detector and the index of refraction of the tissue through which the light travels. Both affect the optical path length. As such, movement of probes for any reason may hinder accurate detection of brain activity if it is not properly compensated for.

An increase in the actual optical path length causes greater absorption. This can lead to overestimation of the change in [Hb] if the path length is assumed to be constant. The phase shift of the detected optical intensity signal is the delay in time of the waveform relative to that of the RF-modulated signal intensity source. High variability of the FD phase shift may indicate inconsistent coupling at the optode-scalp interface, which changes the separation distance and possibly exposes the detector to ambient light, which has no consistent phase shift with respect to the source.

Shifts in the phase can also indicate motion of a probe along the scalp surface. As the probe senses different volumes of tissue, changes in intensity are caused by changes in the optical scattering and absorptive properties of the tissue. If the phase and [Hb] changes are correlated, the [Hb]

changes are likely due to motion-induced changes in path length or absorption. This is because the increased phase indicates a larger path length, which causes more absorption, lowers the detected intensity, and increases the calculated [Hb]. If the phase is steady, the calculated [Hb] changes are likely due to activations of interest, systemic physiology, or detector gain changes. Thus, the phase can be monitored to automate signal removal or alert the user to reset the probe.

The filter of some embodiments assumes that the phase does not change significantly with physiological activation. Neuron swelling or the influx of new hematocytes may affect the scattering, and thus the optical path length and phase. However, this does not occur on time scales accessible to conventional FD instrumentation. Some embodiments may also be used to detect motion artifacts on probes and reduce the artifacts while they are being used to concurrently measure such fast optical signals. The filtering method employed in some embodiments is most appropriate for the frequency domain multiple distance (FDMD) method, where FD instrumentation is used to calculate optical absorption and scattering properties so absolute [Hb] values can be determined. In this case, the filter may be applied to the measured optical intensity, and anti-correlation between the phase and the intensity could be used.

In cases where relative measures suffice, but probe footprints on the head must be small and the signals must be reliable, some embodiments can be used to filter the relative [Hb] changes calculated using the modified Beer Lambert law. The phase signal used should be for the wavelength that matches the [Hb] species of the trace being filtered. This is the case presented herein.

The Kalman Filter and its Suitability

Kalman filtering is a technique for estimating the state of a linear discrete dynamic system. The Kalman filtering implementation used in some embodiments assumes that the unknown true value $x_k$ and measurement value $z_k$ of a system at a time k is determined by the model $$X_k = Ax_{k-1} + w_{k-1} \quad (1)$$

$$z_k = Hx_k + v_k' \quad (2)$$

where A and H are known linear operators. A and H are each assumed to be an identity operator herein. This way, it can be assumed that the process under study is simply the contamination of the data by additive noise. The variables $w_k$ and $v_k$ are process and measurement noise, respectively. The distributions of these two noise sources are assumed to be $$w_k \sim N(0,Q) \text{ and } v_k \sim N(0,R) \quad (3)$$

where $N(\mu,\sigma^2)$ is a normal probability distribution with mean $\mu$ and variance $\sigma_2$. In Equation (3), the mean is 0 and the standard deviation squared is Q. Thus, the variance is Q since variance is the square of the standard deviation. The Kalman filter produces estimates by means of the explicit recurrence relations of the data $$\hat{x}_k = \hat{x}_{k-1} + \frac{P_{k-1} + Q}{p_{k-1} + Q + R}(z_k - \hat{x}_{k-1}) \quad (4)$$

and the variance filter $$p_k = \left(1 - \frac{p_{k-1} + Q}{p_{k-1} + Q + R}\right)(p_{k-1} + Q) \quad (5)$$

beginning with the initial condition $\hat{x}_0 = z_0$ and $p_0 = 1$. Due to the explicit nature of these computations, no iterative solver or optimization procedures are required for filter implementation. Furthermore, the computed estimates $\hat{x}_k$ are optimal in the mean squared error sense. More specifically, $$\hat{x}_k = \text{argmin } E(|x_k - \hat{x}_k|^2) \quad (6)$$

for each time k, where E is the mathematical expectation operator. The optimal properties of the Kalman filter estimates along with the simplicity of its implementation make it an excellent choice for the smoothing of fNIRS data traces.

Values for the variances of the process and measurement noise, Q and R, should be determined before the Kalman filter is implemented since they are used in the calculation of each recurrence relation (i.e., each k). These values can be interpreted as tuning parameters for the Kalman filter. A larger measurement noise variance R weights the data estimate and distrusts the measurement to produce a smoother output, while a smaller measurement noise variance R follows the measured signal more closely. Process variance Q can be increased to allow more dynamic changes in the estimate of the system. The phase channel φ associated with a [Hb] channel $\hat{x}$ is a natural choice of information for computing an appropriate value for measurement noise variance R at each time k.

Application of Kalman Filtering to FNIRS

To implement the Kalman filter, measurement noise variance R can be set to a function of the variance in the phase over a window of time prior to that instance. In some embodiments, the function may be non-linear. The use of the phase differentiates over other implementations of Kalman filtering for motion artifact removal. In some embodiments, the tuning parameter R may be set to the variance of the phase in a rolling window of one second prior to the current instance, plus the correlation of the phase with the [Hb] trace being filtered 20 seconds prior, for example. In other words, the filter turns on at 20 seconds. The contributions of the variance and correlation may be linearly scaled. The absolute value of the correlation may be added if it was greater than a threshold of 0.3, for example. Thus only high correlations impact R. This threshold can be raised for less aggressive filtering.

An advantage of this filtering method is that it only comes on when needed according to actual conditions without adding a channel or auxiliary sensor. The phase provides an objective indication of whether [Hb] changes are due to motion without relying only on the [Hb] trace. Also, the phase can be used to indicate data quality for complete removal during post-processing. A disadvantage may be the introduction of time delays. The filter in some embodiments can only change the estimate at a certain speed when on, depending on the value of Q (e.g., a change every time instance to a chance every second). Delays can be on the order of seconds when the filter is on (i.e., anytime R is greater than 0). Filter turnoff delay may also be a problem. Q may be increased and time windows shortened to reduce delays. Speed issues result from the filtering procedure having to compute a summary measure, such as variance, on the phase channel over a short block of time. Thus, the speed is a function of both the size of this block of time and the type of measure computed. Some measures are less sensitive to sample size and variation.

Other methods for real time artifact removal include smoothing, using other signal correlations, or using a moving standard deviation. With smoothing, the unwanted signal is not rejected, and the temporal resolution advantage of fNIRS is eroded in all instances. The Kalman filter can be adjusted to quickly follow non-noisy data by instance. However, smoothing does not introduce delay. It is also possible to remove motion artifacts from fNIRS signals by taking advantage of the anti-correlation between [HbO] and [HbR] inherent in functional activation. However, the phase-based filter removes motion artifacts from both channels intended to measure functional activations and channels for systemic physiology, which lack neural activation. A moving standard deviation measurement on the [Hb] signal itself may be used to detect spikes for removal. However, mechanical changes can degrade the signal via poor coupling, resulting in a relatively flat [Hb] signal. This would not trigger a moving standard deviation detection algorithm.

Parameter Selection

In some embodiments, parameters may be selected empirically to maximize signal retention and artifact rejection. Different scale factors and rolling time window sizes may be explored for both the variance and the correlation. The scale factors may be selected to bring the magnitude of measurement noise variance R into the useful range of 0 to 5. R should generally be small (i.e., close to zero) to allow desired changes in signal to be retained, and R should be relatively large to remove artifacts. For instance, R on the order of 2 or more was found to remove artifacts effectively. See graphs 300, 310 of FIG. 3 at 100-150 seconds.

Figure 3:
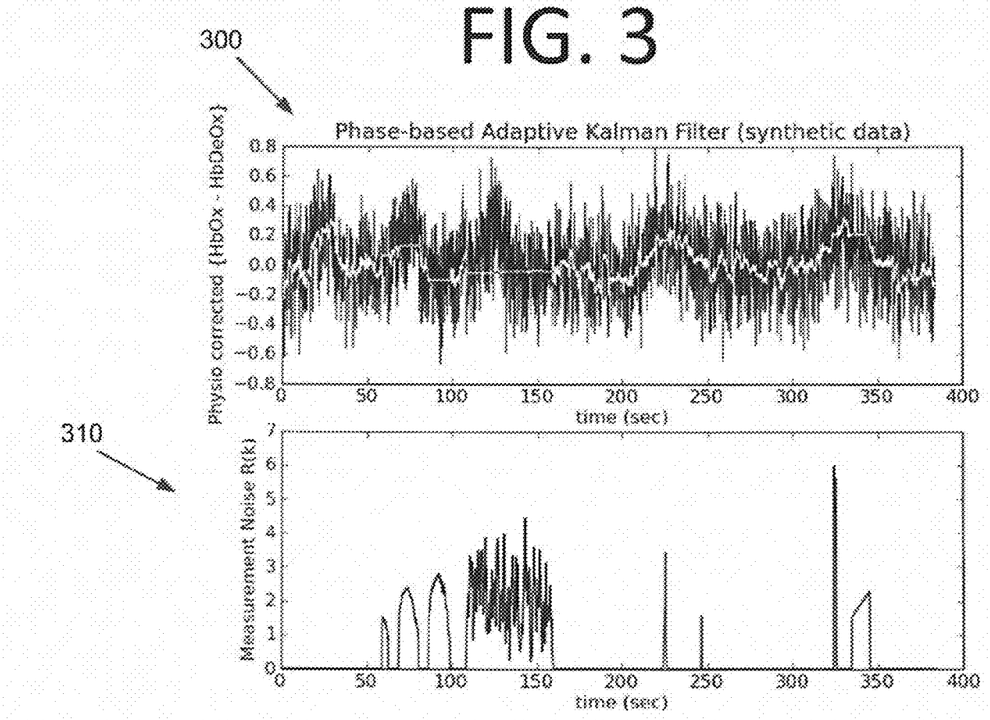
FIG. 3 includes graphs illustrating a calculated R value (bottom) used to filter an [HbO] trace (top) where the filter output is negative, according to an embodiment of the present invention.

Increasing window size increases the signal plateau due to filter turn off delay, as seen in graphs 300, 310 of FIG. 3 at 340 seconds. This is due to the correlation contributing to R even after it has passed in time. This may be tolerable if it is desired to err on the side of signal removal. Shorter windows may be less able to detect artifacts.

Figure 1:
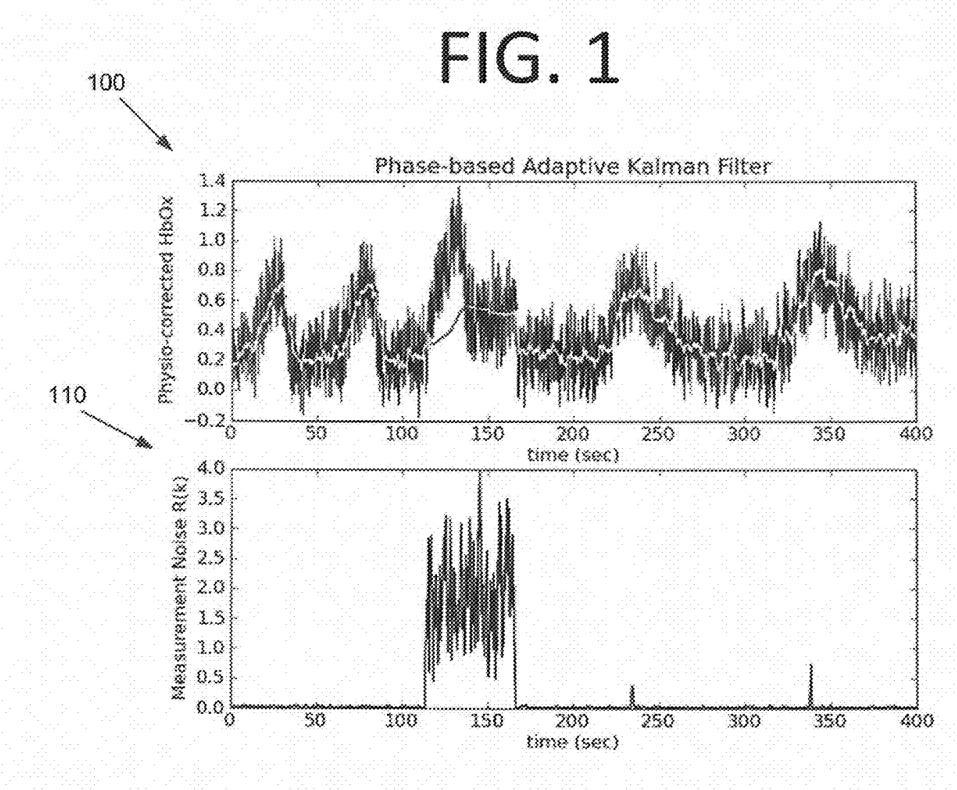
FIG. 1 includes graphs illustrating a calculated R value (bottom) used to filter an [HbO] trace (top) where the filter output is shown in negative color, according to an embodiment of the present invention.
Figure 2:
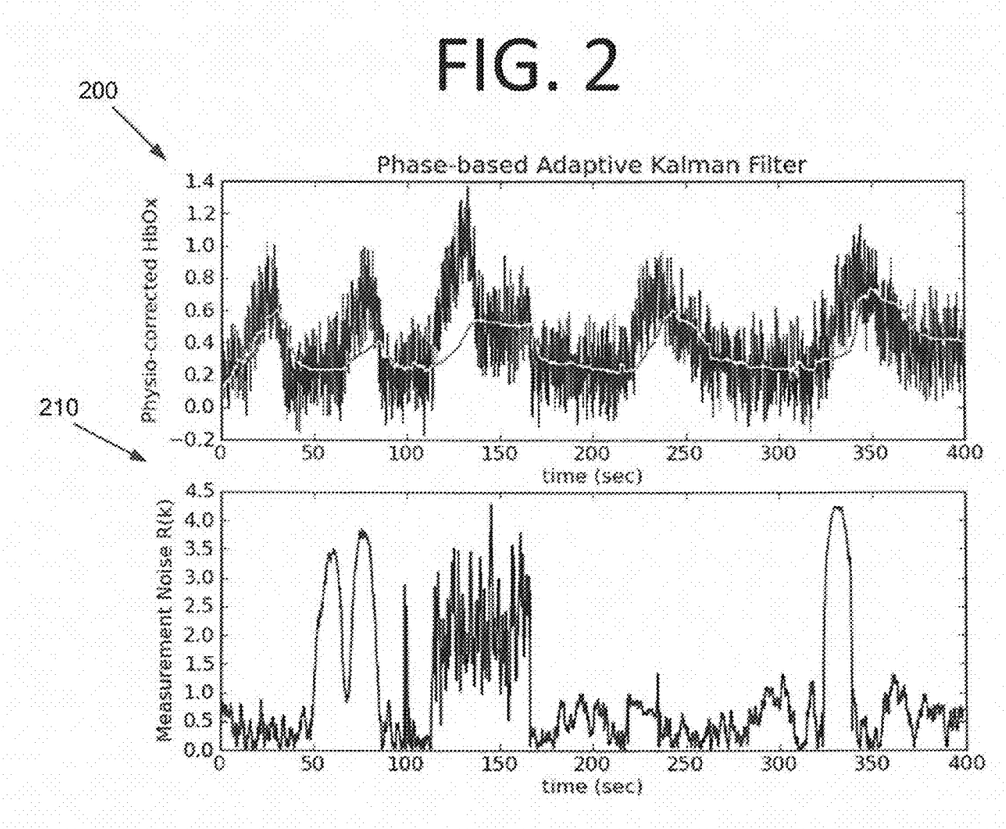
FIG. 2 includes graphs illustrating a calculated R value (bottom) used to filter an [HbO] trace (top) where the filter output is shown in negative color, according to an embodiment of the present invention.

Graphs 100, 110 and 200, 210 of FIGS. 1 and 2 show improved rejection (i.e., signal mean reduction) of the probe slip at 50-100 seconds and the probe relocation at 325 seconds. The artifacts are attained by allowing the correlation to contribute to R. Q was set to 1e-4 in graphs 100, 110, 200, 210 and 1e-5 in graphs 300, 310 of FIGS. 1-3. The phase variance from a rolling window looking back one second was used to calculate R in FIG. 1. Both the phase variance from a rolling window looking back one second and the correlation from a rolling window looking back 20 seconds were used to calculate R in FIG. 2. Both the phase variance and the correlation were used to calculate R in FIG. 3.

If larger, high frequency spikes are not removed. If smaller, desired signal changes are attenuated. The initial state estimate was set to $z_0=0$, and the initial variance of the filter was set to $p_0=1$. These parameters are available for adjustment and optimization, with the objective of maximizing the rejection of artifacts and the retention of good signal.

In real world applications, optimal parameters may depend on source-detector separation. For example, the signal to noise ratio of the phase itself depends on the source-detector separation. Ideally, it may be beneficial for the [HbO] close and far traces and the [HbR] close and far traces to be filtered with their own parameters.

Results

After filtering, the mean of the unwanted peak between 50 seconds and 100 seconds is reduced by 43%. The unwanted peak between 100 seconds and 200 seconds is removed entirely. The reference signal mean is reduced by 9% and the CNR is increased by more than 100% overall. The results are shown in Table 1 below. The filter output trace is shown in graph 300 of FIG. 3.

TABLE 1

PHASE-BASED ADAPTIVE KALMAN FILTER PERFORMANCE BY MOTION TYPE

| Time | Motion Simulated | Phase Shift Signal Feature | Filter Performance Result |
| --- | --- | --- | --- |
| 0-50 s | none (reference) | none (reference) | CNR increase: 125% signal mean reduction: 9% |
| 50-100 s | probe slip | slow changes correlated with [Hb] | unwanted signal mean reduction: 43% |
| 100-200 s | probe decoupling | high variance | unwanted signal mean reduction: 100% |
| 200-300 s | transient probe bump | spike at 225s | CNR increase: 144% signal mean reduction: 12% |
| 300-400 s | probe bump, relocation | spike and step increase at 325 s, correlated with [Hb] | CNR increase: 204% signal mean increase: 11% late filter activation turn off extends activation by 10 s |

Figure 4:
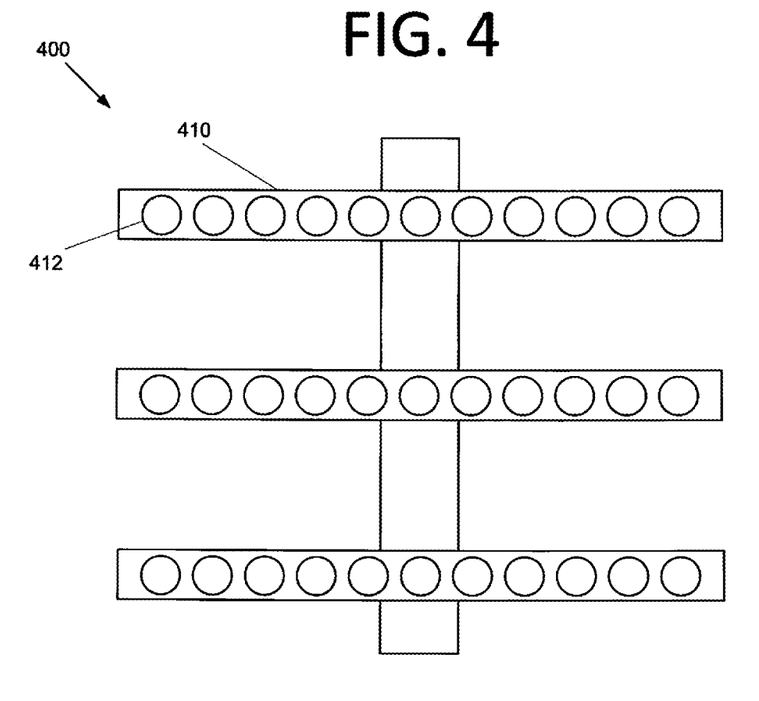
FIG. 4 illustrates a wearable fNIRS sensor array, according to an embodiment of the present invention.

FIG. 4 illustrates a wearable (NIRS sensor array 400, according to an embodiment of the present invention. Sensor array 400 includes multiple bands 410 having probes 412 that are embedded or otherwise attached to bands 410. In some embodiments, either sensor array 400 or another embodiment of a sensor array may be incorporated into a helmet. Further, in other embodiments, the sensor array may have a grid mesh design or have any desired design and configuration that provides sufficient probe input for fNIRS sensing.

Figure 5:
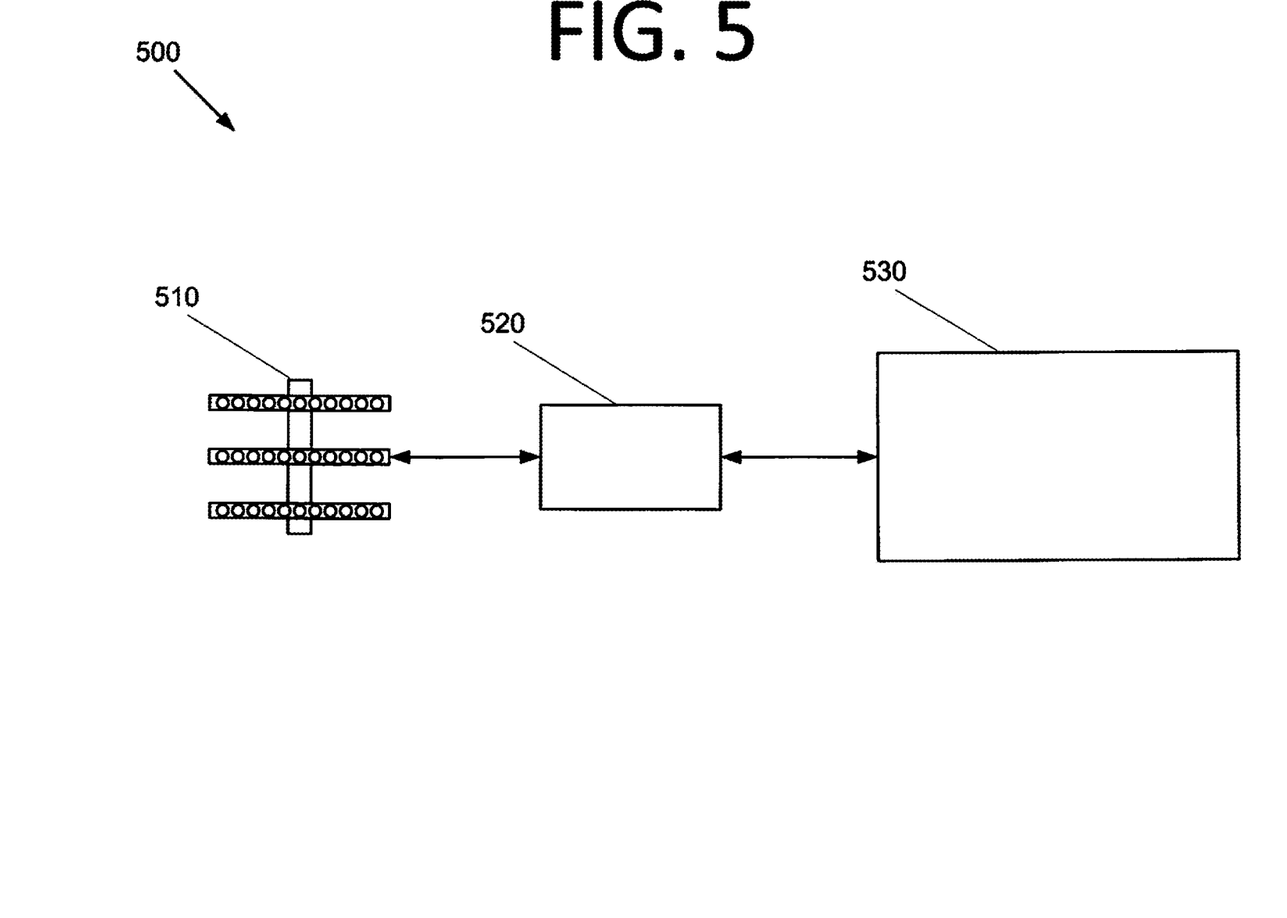
FIG. 5 is an architectural diagram illustrating a fNIRS system, according to an embodiment of the present invention.

FIG. 5 is an architectural diagram illustrating a fNIRS system 500, according to an embodiment of the present invention. fNIRS system 500 includes a wearable fNIRS sensor array 510, a microcontroller 520, and a computing system 530. In some embodiments, microcontroller 520 or computing system 530 may be computing system 700 of FIG. 7, for example. Communications between sensor array 510, microcontroller 520, and computing system 530 may be accomplished wirelessly, via wires, or both. In certain embodiments, all processing may be accomplished by microcontroller 520 and computing system 530 may not be present.

Probes in sensor array 510 detect levels of [Hb] at various sites on a user's head. This data is then periodically sampled by microcontroller 520, which converts analog data from the probes into digital data suitable for processing by computing system 530. The digital data is then provided to computing system 530, which determines [Hb] levels and accounts for noise and phase shifts as discussed above.

Figure 6:
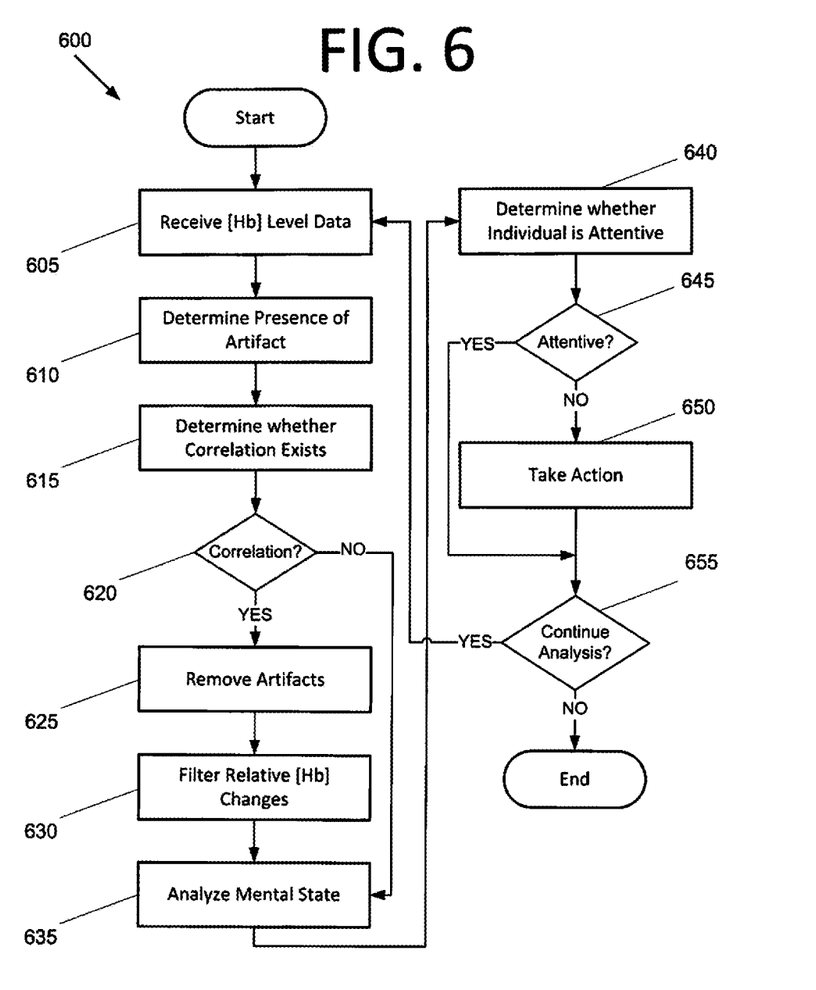
FIG. 6 is a flowchart illustrating a process for performing fNIRS analysis of brain activity, according to an embodiment of the present invention.

FIG. 6 is a flowchart 600 illustrating a process for performing fNIRS analysis of brain activity, according to an embodiment of the present invention. Prior to starting the process, the Kalman filters may be tuned depending on a current state of a process that is being estimated. Values for variances of process noise Q and measurement noise R may be calculated before implementing the Kalman filters, where measurement noise R is set as a function of phase variance over a window of time prior to a current sample. In some embodiments, measurement noise R is in the range of 0 to 5.

The process begins with receiving data pertaining to hemoglobin [Hb] levels in an individual's brain at 605. Presence of a potential artifact based on a phase shift in the data is measured at 610 using frequency-domain (NIRS instrumentation by comparing a signal intensity of a source signal to a detected signal intensity. It is then determined whether changes in the [Hb] levels and changes in the phase shift are correlated at 615. When the changes in the [Hb] levels and the phase shift are not correlated at 620, the process proceeds to step 635, which is discussed below. In other words, the filter turns "off" and no artifact is removed because no actual, correlated artifact was found.

When the changes are correlated at 620, artifacts are removed from the data at 625, leaving signal more indicative of changes due to hemodynamic brain activations. In some embodiments, artifacts are removed when the absolute value of the correlation exceeds a predetermined number. In certain embodiments, the artifacts may include signal contributions from motion, poor probe coupling, or both.

A mental state of the individual is analyzed at 635 based on the measured [Hb] levels in the individual's brain. It is then determined whether the mental state indicates that the individual is attentive enough to perform a task at 640. What mental state constitutes "attentive enough" varies based on the application, and is the subject of ongoing research. For instance, a hemoglobin activation pattern indicative of concentration may be used to determine attentiveness.

Activation patterns are determined by measuring changes in hemoglobin concentration at specific locations in the brain. This is analogous to that commonly done in whole-brain functional magnetic resonance imaging (fMRI) research, except that for fNIRS, the probes should be placed strategically on the head to measure the locations of interest in the cortex of the brain. Activation patterns found to be consistent with the activation of known attentional networks in the brain can indicate attentiveness. It is expected that hemoglobin activation patterns may be used to determine attentiveness through the use of one of many machine learning algorithms including, but not limited to, artificial neural networks, support vector machines, k-nearest neighbors, etc. Such algorithms can be applied to this task by fitting internal parameterization to match the outcomes of experimental data (i.e., "training data"). When the mental state of the individual is attentive enough, the process proceeds to step 655.

However, when the mental state of the individual is not attentive enough to perform the task at 645, action is taken at 650. This action may include sending a signal to a remote individual or entity (e.g., ground control, a corporate officer, a relative, or any other individual entity), generating an audible alarm, or both, for instance. In the case of where the individual is controlling a vehicle, the action may include engaging an autopilot of a vehicle or disabling operation of the vehicle in a controlled manner for ground or sea-based systems. Naturally, disabling a flying vehicle could be catastrophic. The process then proceeds to step 655.

Figure 7:
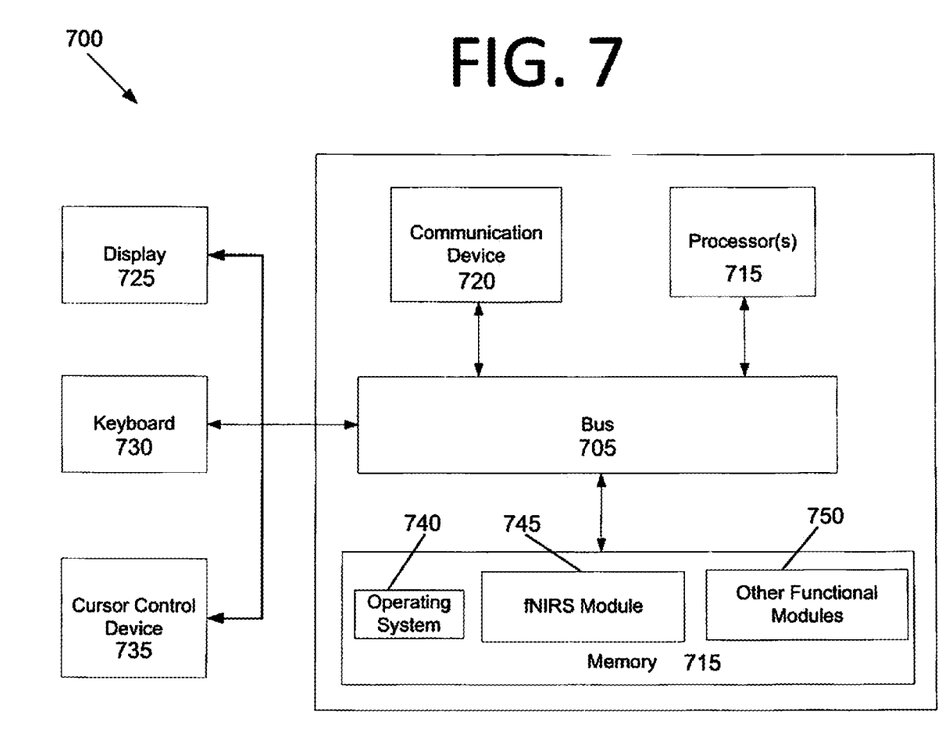
FIG. 7 is a block diagram illustrating a computing system configured to perform fNIRS analysis of brain activity, according to an embodiment of the present invention.

FIG. 7 is a block diagram 700 of a computing system (hereinafter "system") configured to perform MRS analysis of brain activity, according to an embodiment of the present invention. System 700 may be proximate to or remote from the individual being monitored via NIRS, depending on the implementation. System 700 includes a bus 705 or other communication mechanism for communicating information, and processor(s) 710 coupled to bus 705 for processing information. Processor(s) 710 may be any type of general or specific purpose processor, including a central processing unit (CPU) or application specific integrated circuit (ASIC). System 700 further includes a memory 715 for storing information and instructions to be executed by processor(s) 710. Memory 715 can be comprised of any combination of random access memory (RAM), read only memory (ROM), flash memory, cache, static storage such as a magnetic or optical disk, or any other types of non-transitory computer-readable media or combinations thereof. Additionally, system 700 includes a communication device 720, such as a transceiver, to wirelessly communicate with external systems.

Non-transitory computer-readable media may be any available media that can be accessed by processor(s) 710 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 710 are further coupled via bus 705 to a display 725, such as a Liquid Crystal Display (LCD), for displaying information to a user. A keyboard 730 and a cursor control device 735, such as a computer mouse, are further coupled to bus 705 to enable a user to interface with computing system 700. However, in certain embodiments such as those implemented onboard aircraft or in other practical systems, a physical keyboard and mouse may not be present, and computing system 700 may be included as a component of the given system, or otherwise configured to monitor and interact with the given system.

Memory 715 stores software modules that provide functionality when executed by processor(s) 710. The modules include an operating system 740 for system 700. The modules further include an fNIRS module 745 that is configured to provide the fNIRS and artifact removal operations discussed above. System 700 may include one or more additional functional modules 750 that include additional functionality.

One skilled in the art will appreciate that a "system" could be embodied as a computer, a server, a console, an embedded system, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The process steps performed in FIG. 6 may be performed by a computer program, encoding instructions for the non-linear adaptive processor to perform at least the process described in FIG. 6, in accordance with embodiments of the present invention. The computer program may be embodied on a non-transitory computer-readable medium. The computer-readable medium may be, but is not limited to, a hard disk drive, a flash device, a random access memory, a tape, or any other such medium used to store data. The computer program may include encoded instructions for controlling the nonlinear adaptive processor to implement the process described in FIG. 6, which may also be stored on the computer-readable medium.

The computer program can be implemented in hardware, software, or a hybrid implementation. The computer program can be composed of modules that are in operative communication with one another, and which are designed to pass information or instructions to display. The computer program can be configured to operate on a general purpose computer, or an ASIC.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that embodiments of the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A computer-implemented method, comprising:
receiving, by a computing system, data measured using frequency-domain fNIRS instrumentation pertaining to hemoglobin levels in an individual's brain;
determining, by the computing system, presence of a potential artifact based on a phase shift in the data measured using frequency-domain fNIRS instrumentation by comparing a signal intensity of a source signal to a detected signal intensity;
determining, by the computing system, whether changes in the hemoglobin levels and changes in the phase shift are correlated to confirm that the potential artifact is an artifact; and
reducing or removing the artifact, by the computing system, using Kalman filtering when the changes in the hemoglobin levels and changes in the phase shift are correlated.

2. The computer-implemented method of claim 1, wherein said artifacts are detected on probes and reduced while the probes are measuring optical signals.

3. The computer-implemented method of claim 2, wherein said artifacts are removed when an absolute value of the correlation exceeds a predetermined number.

4. The computer-implemented method of claim 2, wherein the artifacts comprise signal contributions from motion, poor probe coupling, or both.

5. The computer-implemented method of claim 2, further comprising:
filtering, by the computing system, relative hemoglobin changes that are calculated using the modified Beer Lambert law.

6. The computer-implemented method of claim 1, further comprising:
tuning the Kalman filters, by the computing system, depending on a current state of a process that is being estimated.

7. The computer-implemented method of claim 1, further comprising:
calculating, by the computing system, values for variances of process noise Q and measurement noise R before implementing the Kalman filters, wherein R is set as a function of phase variance over a window of time prior to a current sample.

8. The computer-implemented method of claim 7, wherein R is in the range of 0 to 5.

9. The computer-implemented method of claim 1, further comprising:
analyzing, by the computing system, a mental state of the individual based on measured hemoglobin levels in the individual's brain; and
determining, by the computing system, whether the mental state indicates that the individual is attentive enough to perform a task.

10. The computer-implemented method of claim 9, wherein when the mental state of the individual is not attentive enough to perform the task, the method further comprises:
sending a signal to a remote individual or entity, generating an audible alarm, or both, by the computing system, indicating that the mental state of the individual is not sufficiently attentive.

11. The computer-implemented method of claim 9, wherein when the mental state of the individual is not attentive enough to perform the task, the method further comprises:
engaging, by the computing system, an autopilot of a vehicle or disabling operation of the vehicle.

12. A computer program embodied on a non-transitory computer-readable medium, the program configured to cause at least one processor to:
receive data pertaining to hemoglobin levels in an individual's brain; and
determine presence of a potential artifact based on a phase shift in the data measured using the sensor array by comparing a signal intensity of a source signal to a detected signal intensity,
determine whether changes in the hemoglobin levels and changes in the phase shift are correlated to confirm that the potential artifact is an artifact, and
reduce or remove the artifact using Kalman filtering when the changes in the hemoglobin levels and changes in the phase shift are correlated
analyze a mental state of the individual based on [measured hemoglobin levels in the individual's brain] the filtered signals; and
determine whether the mental state indicates that the individual is attentive enough to perform a task.

13. The computer program of claim 12, wherein when the mental state of the individual is not attentive enough to perform the task, the program is further configured to cause the at least one processor to send a signal to a remote individual or entity, generate an audible alarm, or both, indicating that the mental state of the individual is not sufficiently attentive.

14. The computer program of claim 12, wherein when the mental state of the individual is not attentive enough to perform the task, the program is further configured to cause the at least one processor to engage an autopilot of a vehicle or disable operation of the vehicle.

15. A system, comprising:
a sensor array configured to provide analog data pertaining to hemoglobin levels in an individual's brain;
a microcontroller configured to receive the analog data from the sensor array and convert the analog data into digital data; and
a computing system configured to receive the digital data from the microcontroller, the computing system configured to:
determine presence of a potential artifact based on a phase shift in the data measured using the sensor array by comparing a signal intensity of a source signal to a detected signal intensity,
determine whether changes in the hemoglobin levels and changes in the phase shift are correlated to confirm that the potential artifact is an artifact, and
reduce or remove the artifact using Kalman filtering when the changes in the hemoglobin levels and changes in the phase shift are correlated.

16. The system of claim 15, wherein the system is integrated with an aircraft, spacecraft, car, truck, ship, or industrial vehicle.

17. The system of claim 15, wherein said artifacts are detected on probes and reduced while the probes are measuring optical signals.

18. The system of claim 15, wherein the computing system is further configured to:
analyze a mental state of the individual based on measured hemoglobin levels in the individual's brain; and
determine whether the mental state indicates that the individual is attentive enough to perform a task.

19. The system of claim 18, wherein when the mental state of the individual is not attentive enough to perform the task, the computing system is further configured to send a signal to a remote individual or entity, generate an audible alarm, or both, indicating that the mental state of the individual is not sufficiently attentive.

20. The system of claim 18, wherein when the mental state of the individual is not attentive enough to perform the task, the computing system is further configured to engage an autopilot of a vehicle or disable operation of the vehicle.

* * * * *